(12) United States Patent
Tian et al.

(10) Patent No.: US 10,640,450 B1
(45) Date of Patent: May 5, 2020

(54) HYDROXYTYROSOL DIHYDROCAFFEATE HAVING ANTIOXIDANT ACTIVITY AND A METHOD FOR PREPARING THE SAME

(71) Applicants: Bin Tian, Xi'an (CN); Xingke Ju, Xi'an (CN); Jingyi Li, Xi'an (CN); Liang Xin, Xi'an (CN); Han Li, Xi'an (CN); Liang Qi, Xi'an (CN); Qianqian Zhao, Xi'an (CN); Yongbo Wang, Xi'an (CN); Dan Yang, Xi'an (CN); Chengyuan Liang, Xi'an (CN); Wenbo Yao, Xi'an (CN)

(72) Inventors: Bin Tian, Xi'an (CN); Xingke Ju, Xi'an (CN); Jingyi Li, Xi'an (CN); Liang Xin, Xi'an (CN); Han Li, Xi'an (CN); Liang Qi, Xi'an (CN); Qianqian Zhao, Xi'an (CN); Yongbo Wang, Xi'an (CN); Dan Yang, Xi'an (CN); Chengyuan Liang, Xi'an (CN); Wenbo Yao, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/724,206

(22) Filed: Dec. 21, 2019

(30) Foreign Application Priority Data

Dec. 11, 2019 (CN) .......................... 2019 1 1262276

(51) Int. Cl.
| | | |
|---|---|---|
| *C07C 69/675* | (2006.01) |
| *C07C 67/08* | (2006.01) |
| *C07C 67/52* | (2006.01) |
| *C07C 67/56* | (2006.01) |
| *B01J 23/652* | (2006.01) |
| *B01J 31/02* | (2006.01) |

(52) U.S. Cl.
CPC .......... *C07C 69/675* (2013.01); *B01J 23/6525* (2013.01); *B01J 31/0247* (2013.01); *C07C 67/08* (2013.01); *C07C 67/52* (2013.01); *C07C 67/56* (2013.01)

(58) Field of Classification Search
CPC ....... C07C 69/675; C07C 67/52; C07C 67/08; C07C 67/56; B01J 23/6525; B01J 31/0247
See application file for complete search history.

(56) References Cited

U.S. PATENT DOCUMENTS

2013/0272983 A1* 10/2013 Okombi .................. A61K 8/42
424/62

OTHER PUBLICATIONS

Yong-Ming Yan, Identification of blapsins A and B as potent small-molecule 14-3-3 inhibitors from the insect Blaps Japanensis, Bioorganic & Medicinal Chemistry Letters 22 (2012) 4179-4181.*

* cited by examiner

*Primary Examiner* — Jafar F Parsa

(57) ABSTRACT

A compound having the formula (I):

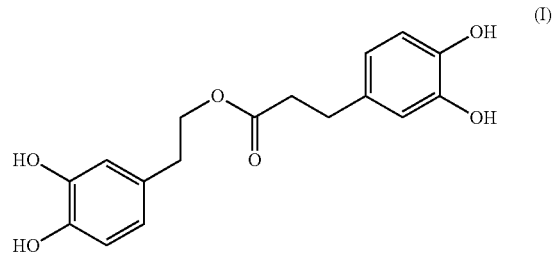

is disclosed. A method of preparing the compound of formula (I) is also disclosed.

12 Claims, 3 Drawing Sheets

HYDROXYTYROSOL DIHYDROCAFFEATE HAVING ANTIOXIDANT ACTIVITY AND A METHOD FOR PREPARING THE SAME

The present invention claims priority to Chinese Patent Application No. CN 201911262276.6, field on Dec. 11, 2019, which is incorporated by reference for all purposes as if fully set forth herein.

FIELD OF THE INVENTION

The present invention relates to food chemistry field, specifically, a hydroxytyrosol dihydrocaffeate having antioxidant activity and a method for preparing the same.

BACKGROUND OF THE INVENTION

Fat, as one of the three main nutrients, is an essential part of the daily diet. Oxidation of oils and fats is an important factor affecting the quality of oils. The automatic oxidation of oils and fats is a complete spontaneous oxidation reaction of activated olefin-containing substrates (such as unsaturated oils) and oxygen in the air at room temperature without any direct illumination or any catalyst. The products of oil oxidation not only affect the flavor and color of oil food and reduce the quality of food, but also produce a lot of toxic substances that affect the health of eaters. The peroxide of oil will damage the membrane, enzymes and proteins, can lead to many diseases of aging, and even cause cancer, seriously endangering human health. In order to prolong the shelf life of oils and fats, the addition of antioxidants to oils and fats is one of the most effective means. However, several commonly used synthetic antioxidants have some hidden dangers, which are strongly opposed by the people in some countries and banned or restricted. The research of antioxidants began to turn to the application of natural antioxidants.

Hydroxytyrosol is a natural polyphenol, which has a variety of biological and pharmacological activities and can be extracted in olive oil. Hydroxytyrosol plays an important role in anti-cancer, anti-inflammation, prevention and treatment of cardiovascular and cerebrovascular diseases, prevention and treatment of coronary heart disease, protection of retinal pigment epithelial cells and so on. The molecular structure of hydroxytyrosol not only has phenolic hydroxyl group like other phenolic substances, but also has alcohol hydroxyl group on the ethanol chain connected with benzene ring. Therefore, hydroxytyrosol has excellent antioxidant activity. By controlling the oxidation of many unsaturated fatty acids, exogenous and endogenous oxides and free radicals can be effectively removed. As a food additive, it can promote human health and increase the antioxidant capacity of food. At the same time, hydroxytyrosol is highly hydrophilic.

Dihydrocaffeic acid, also known as 3, 4-dihydroxyphenyl propionic acid, can be extracted and separated from *Eucommia ulmoides, Salvia miltiorrhiza*, artichoke, *Atractylodes macrocephala* and Lianqincao. It is a phenolic acid with catechol structure.

In the present invention, dihydrocaffeic acid is modified by the hydroxytyrosol structure to obtain a hydroxytyrosol dihydrocaffeate. Antioxidant experiment shows that the hydroxytyrosol dihydrocaffeate has excellent antioxidant activity and high medical research and application value in the field of antioxidant health products.

SUMMARY OF THE INVENTION

In one embodiment, the present invention provides a compound having the following formula (I):

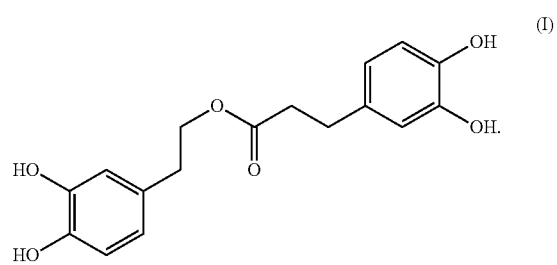 [SMILES: O=C(CCc1ccc(O)c(O)c1)OCCc1ccc(O)c(O)c1]

In another embodiment, the present invention provides a method of preparing the compound of formula (I). The method includes reacting a compound of formula (II) with a compound of formula (III) in an organic solvent to obtain the compound of formula (I):

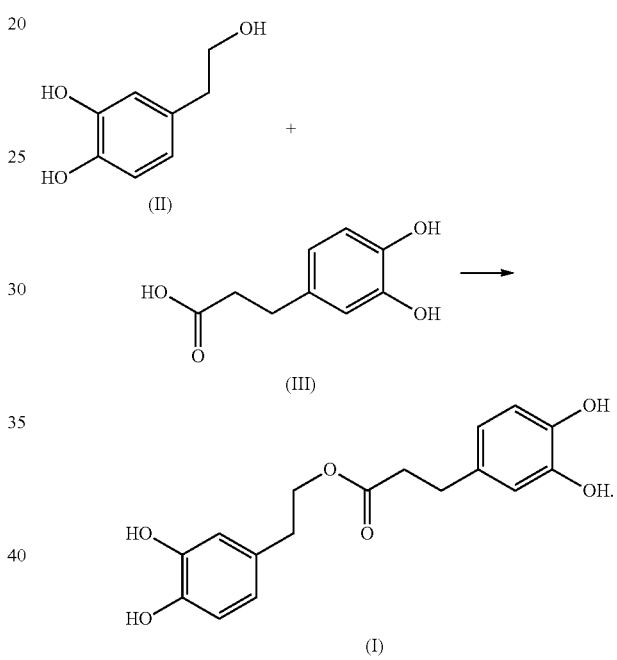

In another embodiment, the reaction of the compound of formula (II) with the compound of formula (III) includes the following steps: placing the compound of formula (II), a catalyst, and an organic solvent in a reactor under nitrogen atmosphere, the catalyst being EDC; adding the compound of formula (III) to the reactor to form a reaction mixture; heating the reaction mixture at 50-85° C. for 1-4 hours; concentrated the reaction mixture to obtain a crude product; and purifying the crude product by a silica gel column, eluting with an ethyl acetate/petroleum ether solvent as an eluent, to obtain the compound of formula (I).

In another embodiment, the organic solvent is toluene, ethyl acetate, or acetonitrile.

In another embodiment, the compound of formula (II) and the compound (III) have a molar ratio of 1:1 to 1:1.3.

In another embodiment, the molar ratio is 1:1.1.

In another embodiment, the reaction mixture is heated at 75° C. for 4 hours;

In another embodiment, the ethyl acetate/petroleum ether solvent has a ethyl acetate:petroleum volume ratio of 3:10.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 25-50° C. for 5-10 hours; placing the reaction mixture in a separating funnel to separate a crude product; and purifying the crude product by recrystallization in methanol to obtain the compound of formula (I).

In another embodiment, the ionic liquid is 1-butyl-3-methylimidazolium tetrafluoroborate ([BMIM][$BF_4$]).

In another embodiment, the compound of formula (II) and the compound (III) have a molar ratio of 1:1 to 1:1.3.

In another embodiment, the molar ratio is 1:1.1.

In another embodiment, the reaction mixture is heated at 25° C. for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of Compound 3,4-dihydroxyphenethyl 3-(3,4-dihydroxyphenyl)propanoate (hydroxytyrosol dihydrocaffeate, compound of formula (I))

In a 100 mL three-necked flask, 100.2 mg (0.65 mmol) of hydroxytyrosol and 124 mg (0.65 mmol) of EDC (1-ethyl-3-(3-dimethylaminopropyl)carbodiimide) were dissolved in 50 mL of acetonitrile under nitrogen atmosphere to form a reaction mixture. 129.3 mg (0.71 mmol) of dihydrocaffeic acid was dissolved in 15 mL of acetonitrile, and then was added dropwise to the reaction mixture by a separatory funnel. After the completion of the dropwise addition, the temperature of the reaction mixture was raised to 75° C., and the reaction was carried out for 4 hours. Thin layer chromatography was used to track the reaction to completion, heating was stopped, and the protective device was removed. The reaction mixture was concentrated, washed with water, extracted with ethyl acetate. Ethyl acetate was dried and concentrated to give a crude product of hydroxytyrosol dihydrocaffeate. The crude product was further purified by silica gel column chromatography eluting with petroleum ether:ethyl acetate=3:10 as eluent to obtain 150.2 mg of purified hydroxytyrosol dihydrocaffeate, a total yield of 72.65%.

Figure 2:
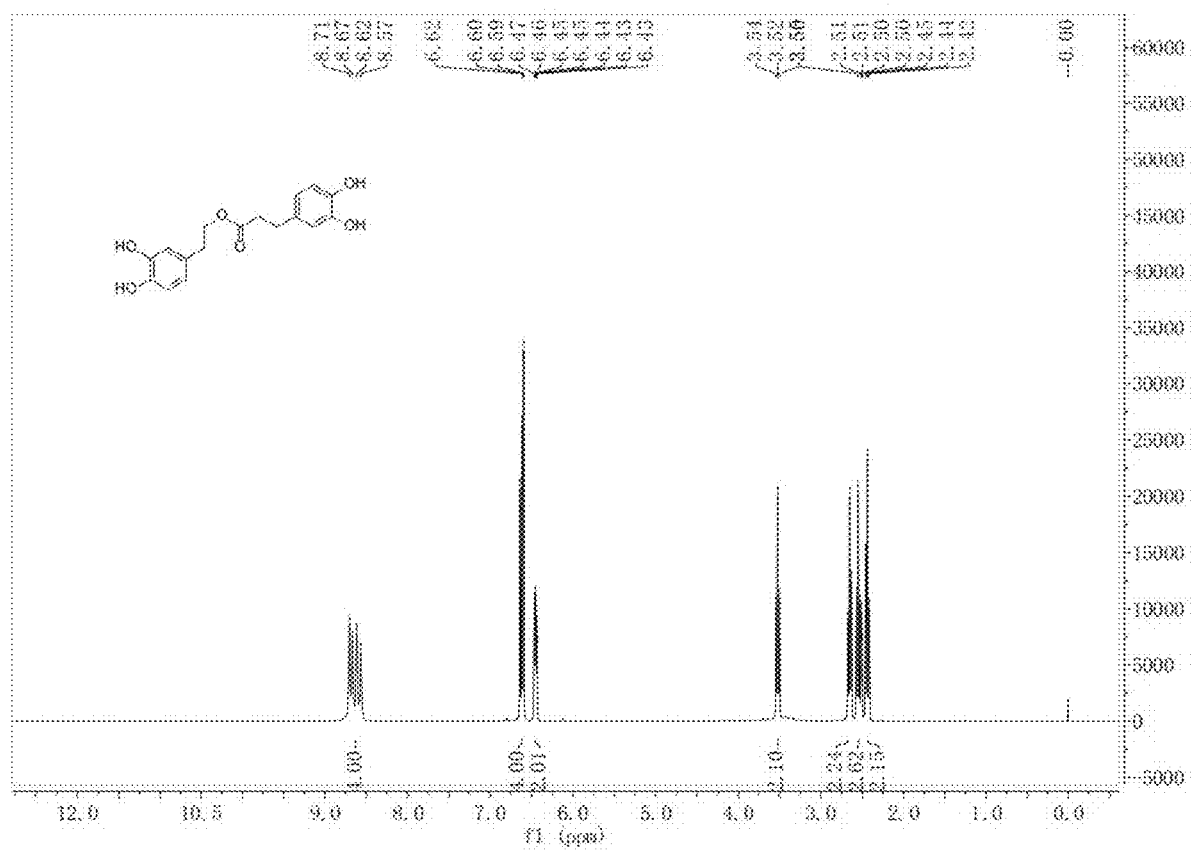
FIG. 2 is the $^1$HNMR spectrum of the hydroxytyrosol dihydrocaffeate.
Figure 3:
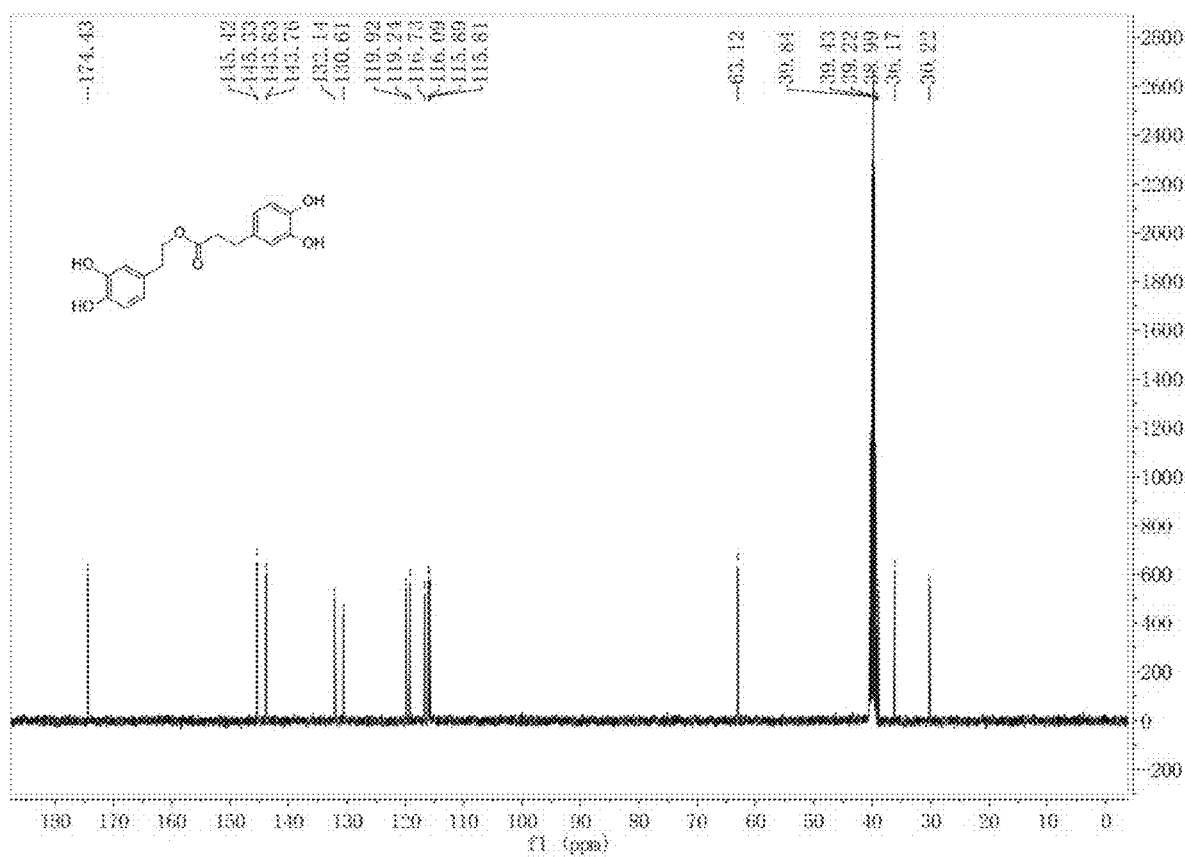
FIG. 3 is the $^{13}$CNMR spectrum of the hydroxytyrosol dihydrocaffeate.

$^1$H-NMR (400 MHz, DMSO-$d_6$) δ (ppm): 8.64 (4H, d), 6.62 (4H, m), 6.45 (2H, m), 3.52 (2H, t), 2.65 (2H, t), 2.52 (2H, d), 2.44 (2H, t); $^{13}$C-NMR (400 MHz, DMSO-$d_6$) δ (ppm): 174.4, 145.3, 143.8, 132.1, 130.6, 119.9, 119.2, 116.7, 116.0, 115.8, 115.1, 63.1, 36.1, 30.2. The $^1$H-NMR spectrum is shown in FIG. 2; and the $^{13}$C-NMR spectrum is shown in FIG. 3.

Example 2

Preparation of Compound 3,4-dihydroxyphenethyl 3-(3,4-dihydroxyphenyl)propanoate In a 100 mL three-necked flask, 120.3 mg (0.78 mmol) of hydroxytyrosol and 124 mg (0.65 mmol) of EDC were dissolved in 50 mL of toluene under nitrogen atmosphere to form a reaction mixture. 129.3 mg (0.71 mmol) of dihydrocaffeic acid was dissolved in 15 mL of toluene, and then was added dropwise to the reaction mixture by a separatory funnel. After the completion of the dropwise addition, the temperature of the reaction mixture was raised to 60° C., and the reaction was carried out for 3 hours. Thin layer chromatography was used to track the reaction to completion, heating was stopped, and the protective device was removed. The reaction mixture was concentrated, washed with water, extracted with ethyl acetate. Ethyl acetate was dried and concentrated to give a crude product of hydroxytyrosol dihydrocaffeate. The crude product was further purified by silica gel column chromatography eluting with petroleum ether:ethyl acetate=3:10 as eluent to obtain 115.2 mg of purified hydroxytyrosol dihydrocaffeate, a total yield of 55.72%.

Example 3

Preparation of Compound 3,4-dihydroxyphenethyl 3-(3,4-dihydroxyphenyl)propanoate In a 100 mL three-necked flask, 100.2 mg (0.65 mmol) of hydroxytyrosol and 124 mg (0.65 mmol) of EDC were dissolved in 50 mL of tetrahydrofuran under nitrogen atmosphere to form a reaction mixture. 153.0 mg (0.84 mmol) of dihydrocaffeic acid was dissolved in 15 mL of tetrahydrofuran, and then was added dropwise to the reaction mixture by a separatory funnel. After the completion of the dropwise addition, the temperature of the reaction mixture was raised to 50° C., and the reaction was carried out for 4 hours. Thin layer chromatography was used to track the reaction to completion, heating was stopped, and the protective device was removed. The reaction mixture was concentrated, washed with water, extracted with ethyl acetate. Ethyl acetate was dried and concentrated to give a crude product of hydroxytyrosol dihydrocaffeate. The crude product was further purified by silica gel column chromatography eluting with petroleum ether:ethyl acetate=3:10 as eluent to obtain 120.6 mg of purified hydroxytyrosol dihydrocaffeate, a total yield of 58.32%.

Example 4

Preparation of Compound 3,4-dihydroxyphenethyl 3-(3,4-dihydroxyphenyl)propanoate In a 100 mL three-necked flask, 100.2 mg (0.65 mmol) of hydroxytyrosol and 124 mg (0.65 mmol) of EDC were dissolved in 50 mL of toluene under nitrogen atmosphere to form a reaction mixture. 129.3 mg (0.71 mmol) of dihydrocaffeic acid was dissolved in 15 mL of toluene, and then was added dropwise to the reaction mixture by a separatory funnel. After the completion of the dropwise addition, the temperature of the reaction mixture was raised to 65° C., and the reaction was carried out for 2 hours. Thin layer chromatography was used to track the reaction to completion, heating was stopped, and the protective device was removed. The reaction mixture was concentrated, washed with water, extracted with ethyl acetate. Ethyl acetate was dried and concentrated to give a crude product of hydroxytyrosol dihydrocaffeate. The crude product was further purified by silica gel column chromatography eluting with petroleum ether:ethyl acetate=3:10 as eluent to obtain 127.9 mg of purified hydroxytyrosol dihydrocaffeate, a total yield of 61.87%.

Example 5

Preparation of Compound 3,4-dihydroxyphenethyl 3-(3,4-dihydroxyphenyl)propanoate In a 100 mL three-necked flask, 100.2 mg (0.65 mmol) of hydroxytyrosol and 124 mg (0.65 mmol) of EDC were dissolved in 50 mL of acetonitrile under nitrogen atmosphere to form a reaction mixture. 118.4 mg (0.65 mmol) of dihydrocaffeic acid was dissolved in 15 mL of acetonitrile, and then was added dropwise to the reaction mixture by a separatory funnel. After the completion of the dropwise addition, the temperature of the reaction mixture was raised to 60° C., and the reaction was carried out for 3 hours. Thin layer chromatography was used to track the reaction to completion, heating was stopped, and the protective device was removed. The reaction mixture was concentrated, washed with water, extracted with ethyl acetate. Ethyl acetate was dried and concentrated to give a crude product of hydroxytyrosol dihydrocaffeate. The crude product was further purified by silica gel column chromatography eluting with petroleum ether:ethyl acetate=3:10 as eluent to obtain 139.5 mg of purified hydroxytyrosol dihydrocaffeate, a total yield of 67.46%.

Example 6

Preparation of Compound 3,4-dihydroxyphenethyl 3-(3,4-dihydroxyphenyl)propanoate In a 100 mL three-necked flask, 100.2 mg (0.65 mmol) of hydroxytyrosol and 124 mg (0.65 mmol) of EDC were dissolved in 50 mL of tetrahydrofuran under nitrogen atmosphere to form a reaction mixture. 153.0 mg (0.84 mmol) of dihydrocaffeic acid was dissolved in 15 mL of tetrahydrofuran, and then was added dropwise to the reaction mixture by a separatory funnel. After the completion of the dropwise addition, the temperature of the reaction mixture was raised to 55° C., and the reaction was carried out for 4 hours. Thin layer chromatography was used to track the reaction to completion, heating was stopped, and the protective device was removed. The reaction mixture was concentrated, washed with water, extracted with ethyl acetate. Ethyl acetate was dried and concentrated to give a crude product of hydroxytyrosol dihydrocaffeate. The crude product was further purified by silica gel column chromatography eluting with petroleum ether:ethyl acetate=3:10 as eluent to obtain 93.4 mg of purified hydroxytyrosol dihydrocaffeate, a total yield of 45.18%.

Example 7

Preparation of Compound 3,4-dihydroxyphenethyl 3-(3,4-dihydroxyphenyl)propanoate In a 100 mL three-necked flask, 100.2 mg (0.65 mmol) of hydroxytyrosol, 129.3 mg (0.71 mmol) of dihydrocaffeic acid, and 12.0 mg (0.007 mmol) 12-molybdosilicic acid hydrate ($H_6Mo_{12}O_{41}Si$) were dissolved in 50 mL of an ionic liquid (1-butyl-3-methylimidazolium tetrafluoroborate ([BMIM][BF$_4$])) under nitrogen atmosphere to form a reaction mixture. The reaction mixture was reacted at 25° C. for 8 hours. Thin layer chromatography was used to track the reaction to completion, heating was stopped, and the protective device was removed. The reaction mixture was transferred to a separatory funnel. An ester layer was separated from the ionic liquid layer. The ester layer contained the crude product. The crude product was recrystallized in 50 mL methane to obtain 170.2 mg of purified hydroxytyrosol dihydrocaffeate, a total yield of 82.34%.

Example 8

Preparation of Compound 3,4-dihydroxyphenethyl 3-(3,4-dihydroxyphenyl)propanoate In a 100 mL three-necked flask, 100.2 mg (0.65 mmol) of hydroxytyrosol, 129.3 mg (0.71 mmol) of dihydrocaffeic acid, and 12.0 mg (0.007 mmol) 12-molybdosilicic acid hydrate ($H_6Mo_{12}O_{41}Si$) were dissolved in 50 mL of an ionic liquid (1-butyl-3-methylimidazolium tetrafluoroborate ([BMIM][BF$_4$])) under nitrogen atmosphere to form a reaction mixture. The reaction mixture was reacted at 50° C. for 4 hours. Thin layer chromatography was used to track the reaction to completion, heating was stopped, and the protective device was removed. The reaction mixture was transferred to a separatory funnel. An ester layer was separated from the ionic liquid layer. The ester layer contained the crude product. The crude product was recrystallized in 50 mL methane to obtain 156.2 mg of purified hydroxytyrosol dihydrocaffeate, a total yield of 75.54%.

Example 9

The Antioxidant Activity of Hydroxytyrosol Dihydrocaffeate Measured by DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —NO$_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

(a) Preparation of DPPH solution: measuring exact amount of 2,2-diphenyl-1-picryl hydrazyl (DPPH) and dissolving in toluene to prepare a 0.2 mmoL/L DPPH solution, stored at 0° C. in dark.

(b) Preparation of test solution: Vc (vitamin C, positive control), hydroxytyrosol dihydrocaffeate (sample), hydroxytyrosol (control) and dihydrocaffeic acid (control). The sample solution was subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 1).

TABLE 1

Dilution Gradient of the Test Solutions

| Number | Test solution | Concentration gradient/ppm |
|---|---|---|
| Vc | Vitamin C | 1.76, 8.80, 21.12, 42.24, 79.20, 112.64, 281.60, 492.80, 792.00, 915.20 |
| A | Hydroxytyrosol dihydrocaffeate | 1.76, 8.80, 21.12, 42.24, 79.20, 112.64, 281.60, 492.80, 792.00, 915.20 |
| B | Hydroxytyrosol | 1.76, 8.80, 21.12, 42.24, 79.20, 112.64, 281.60, 492.80, 792.00, 915.20 |
| C | Dihydrocaffeic acid | 1.76, 8.80, 21.12, 42.24, 79.20, 112.64, 281.60, 492.80, 792.00, 915.20 |

(c) Specific steps:

Sample liquid absorbance measurement: Taking 2 mL of test solution (Table 1: Vc, A, B, C), adding 2 mL of DPPH solution with concentration of $2*10^4$ moL/L, mixing and reacting in the dark at room temperature for 30 min, adjusting to zero with toluene, and measuring at 517 nm. The absorbance $A_i$ was simultaneously measured for the absorbance of 2 mL of toluene mixed with 2 mL of the solution and the absorbance $A_0$ of 2 mL of DPPH solution mixed with 2 mL of toluene (The experimental results are shown in Table 2).

TABLE 2

Absorbance Test Results of Each Test Solution

| Sample | Absorbance | 1.76 | 8.80 | 21.12 | 42.24 | 79.20 | 112.64 | 281.60 | 492.80 | 792.00 | 915.20 |
|---|---|---|---|---|---|---|---|---|---|---|---|
| Vc | $A_i$ | 0.718 | 0.624 | 0.222 | 0.142 | 0.091 | 0.078 | 0.076 | 0.070 | 0.074 | 0.065 |
|  | $A_j$ | 0.068 | 0.061 | 0.050 | 0.054 | 0.069 | 0.057 | 0.062 | 0.062 | 0.066 | 0.059 |
|  | $A_0$ |  |  |  |  |  | 0.846 |  |  |  |  |
| A | $A_i$ | 0.720 | 0.689 | 0.579 | 0.515 | 0.292 | 0.209 | 0.198 | 0.166 | 0.135 | 0.114 |
|  | $A_j$ | 0.045 | 0.041 | 0.060 | 0.063 | 0.059 | 0.057 | 0.059 | 0.053 | 0.049 | 0.045 |
|  | $A_0$ |  |  |  |  |  | 0.789 |  |  |  |  |
| B | $A_i$ | 0.918 | 0.904 | 0.810 | 0.739 | 0.630 | 0.580 | 0.403 | 0.365 | 0.268 | 0.254 |
|  | $A_j$ | 0.053 | 0.046 | 0.047 | 0.039 | 0.060 | 0.055 | 0.041 | 0.046 | 0.035 | 0.037 |
|  | $A_0$ |  |  |  |  |  | 0.935 |  |  |  |  |
| C | $A_i$ | 0.952 | 0.934 | 0.878 | 0.820 | 0.709 | 0.652 | 0.489 | 0.431 | 0.336 | 0.321 |
|  | $A_j$ | 0.051 | 0.042 | 0.046 | 0.043 | 0.059 | 0.055 | 0.040 | 0.044 | 0.038 | 0.035 |
|  | $A_0$ |  |  |  |  |  | 0.962 |  |  |  |  |

The clearance rate is calculated using the formula below, and the results are shown in Table 3 and FIG. 1.

Clearance calculation: Clearance rate (%) = $[1-(A_i-A_j)/A_0]*100\%$

TABLE 3

DPPH Clearance Rate Experiment Results

| Concentration/ppm | Clearance rate/% (n = 3) | | | |
|---|---|---|---|---|
|  | Vc | A | B | C |
| 1.76 | 23.16 | 13.45 | 7.42 | 6.27 |
| 8.80 | 33.47 | 17.80 | 8.16 | 7.46 |

TABLE 3-continued

DPPH Clearance Rate Experiment Results

| Concentration/ppm | Clearance rate/% (n = 3) | | | |
|---|---|---|---|---|
|  | Vc | A | B | C |
| 21.12 | 79.63 | 34.16 | 18.43 | 13.42 |
| 42.24 | 89.55 | 42.74 | 25.10 | 19.21 |
| 79.20 | 97.42 | 70.42 | 38.99 | 32.36 |
| 112.64 | 97.53 | 80.63 | 43.87 | 37.87 |
| 281.60 | 98.29 | 82.35 | 61.25 | 53.23 |
| 492.80 | 99.06 | 85.70 | 65.88 | 59.82 |
| 792.00 | 99.10 | 89.10 | 75.03 | 69.01 |
| 915.20 | 99.28 | 91.22 | 76.76 | 70.28 |

Figure 1:
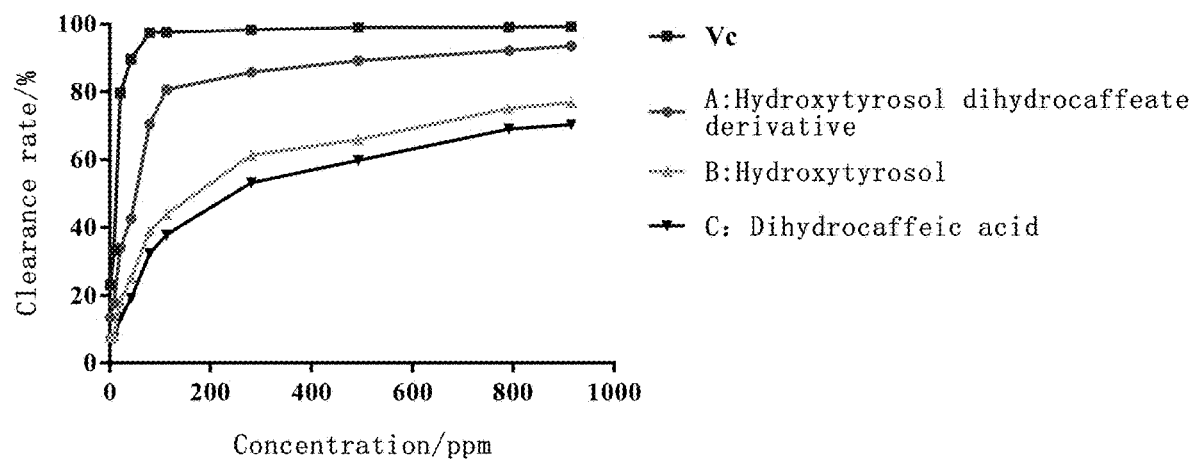
FIG. 1 shows the scavenging activity of the sample and control solutions at different concentrations.

As shown in FIG. 1 and Table 1-3, the antioxidant activity of hydroxytyrosol dihydrocaffeate (A) showed a concentration-dependent relationship, and the scavenging ability of hydroxytyrosol dihydrocaffeate (A) to DPPH radical increased with the increase of concentration. In the determined concentration range, the highest scavenging rate of DPPH radical was 91.22%, similar to the scavenging activity of Vc (vitamin C). Compared with the control group treated with hydroxytyrol (B) and dihydrocaffeic acid (C) alone, the scavenging ability of hydroxytyrosol dihydrocaffeate (A) is much higher than those of hydroxytyrosol (B) control group and dihydrocaffeic acid (C) control groups. The experimental results show that hydroxytyrosol dihydrocaffeate (A) has excellent antioxidant activity and a good application prospect in food, cosmetics, nutritional products, and pharmaceuticals.

What is claimed is:

1. A method of preparing a compound having the following formula (I):

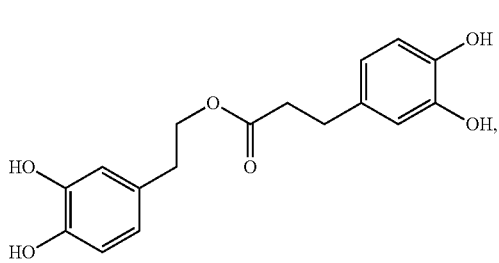

comprising:
reacting a compound of formula (II) with a compound of formula (III) in an organic solvent to obtain the compound of formula (I):

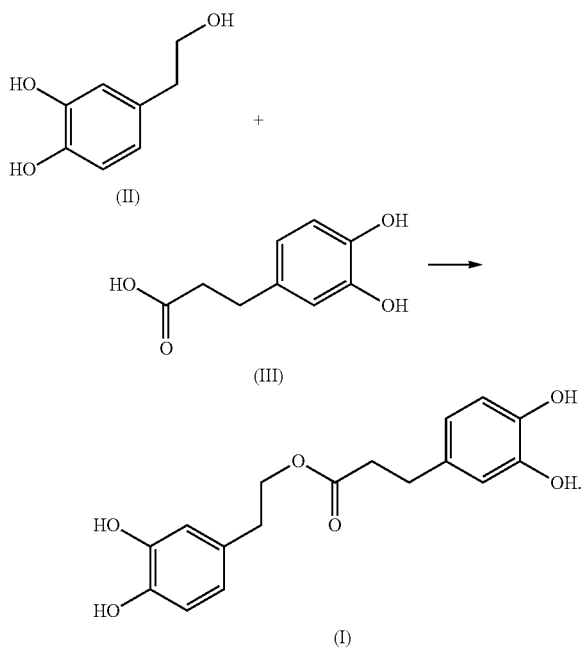

2. The method of claim 1, wherein the reaction of the compound of formula (II) with the compound of formula (III) comprises the following steps:
placing the compound of formula (II), a catalyst, and an organic solvent in a reactor under nitrogen atmosphere, the catalyst being EDC;
adding the compound of formula (III) to the reactor to form a reaction mixture;
heating the reaction mixture at 50-85° C. for 1-4 hours;
concentrated the reaction mixture to obtain a crude product; and
purifying the crude product by a silica gel column, eluting with an ethyl acetate/petroleum ether solvent as an eluent, to obtain the compound of formula (I).

3. The method of claim 2, wherein the organic solvent is toluene, ethyl acetate, or acetonitrile.

4. The method of claim 2, wherein the compound of formula (II) and the compound (III) have a molar ratio of 1:1 to 1:1.3.

5. The method of claim 4, wherein the molar ratio is 1:1.1.

6. The method of claim 2, wherein the reaction mixture is heated at 75° C. for 4 hours.

7. The method of claim 2, wherein the ethyl acetate/petroleum ether solvent has a ethyl acetate:petroleum volume ratio of 3:10.

8. The method of claim 1, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 25-50° C. for 5-10 hours;
placing the reaction mixture in a separating funnel to separate a crude product; and
purifying the crude product by recrystallization in methanol to obtain the compound of formula (I).

9. The method of claim 8, wherein the ionic liquid is 1-butyl-3-methylimidazolium tetrafluoroborate ([BMIM][BF$_4$]).

10. The method of claim 8, wherein the compound of formula (II) and the compound (III) have a molar ratio of 1:1 to 1:1.3.

11. The method of claim 10, wherein the molar ratio is 1:1.1.

12. The method of claim 8, wherein the reaction mixture is heated at 25° C. for 8 hours.

* * * * *